US006319890B1

(12) United States Patent
Dierich et al.

(10) Patent No.: US 6,319,890 B1
(45) Date of Patent: *Nov. 20, 2001

(54) INHIBITION OF BINDING OF COMPLEMENT FACTOR H

(76) Inventors: Manfred P. Dierich, Karl-Innerebner-Strasse 43, A-6020 Innsbruck (AT); Alberto Clivio, Via San Lorenzo 2, I-21030 Orino (VA) (IT); Heribert Stoiber, Mentlgasse 7/13, A-6020 Innsbruck (AT)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/775,496

(22) Filed: Dec. 30, 1996

(51) Int. Cl.[7] .................... A61K 38/08; A61K 38/12; C07K 7/06; C07K 7/64
(52) U.S. Cl. .................... 514/2; 514/9; 514/10; 514/11; 514/12; 514/13; 514/14; 514/17; 530/317; 530/324; 530/325; 530/326; 530/327; 530/328; 530/329; 530/330; 530/350
(58) Field of Search .................... 530/350, 317, 530/324, 325, 326, 327, 328, 329, 330; 514/2, 9–14, 17

(56) References Cited

U.S. PATENT DOCUMENTS 5,472,939 * 12/1995 Fearon et al. .................... 514/8
6,074,645 * 6/2000 Diamond et al. .................... 424/186.1

FOREIGN PATENT DOCUMENTS

WO 95/07354  3/1995  (WO) .................... C12N/15/48

OTHER PUBLICATIONS

Lellouch et al., Biochemiistry vol. 31 pp. 2279–2285, 1992.*
Ripoche et al., "The Complete Amino Acid Sequence of Human Complement Factor H", Biochem J., (1988), v. 593, pp. 593–602.*
Journal of Biological Chemistry, vol. 266, No. 25, Sep. 5, 1991, MD US, pp. 16847–16853, MK Pangburn et al.: "Localization of heparin–binding site on complement factor H".
Proccedings of the National Academy of Sciences of USA, vol. 93, No. 20, Oct. 1, 1996, Washington US pp. 10996–11001, AK Sharma & MK Pangburn: "Identification of three physically and functionally distinct binding sites for C3b in human complement factor H by deletion mutagenesis".
AIDS Research and Human Retroviruses, vol. 11, No. 8, Nov. 1995, pp. 971–980, Mary Ann Liebert Inc., New York, USA, C Pinter et al.: "HIV glyprotein 41 and complement factor H interact with each other and share functional as well as antigenic homology".
AIDS Research and Human Retrovirus, vol. 11, No. 5, May 1995, Mary Ann Liebert Inc., New York, USA, pp. 577–588, C Pinter et al.: "Direct interaction of complement factor H with the domain of HIV type I glycoprotein 120".
Journal of Immunology, vol. 157, No. 12, Dec. 15, 1996, pp. 5422–5427, TK Blackmore et al.: "Identification of a heparin binding domain in the seventh short consensus repeat of complement factor H".
Eur. J. Immunology, vol. 25, 1995, pp. 285–290, P. Marschang et al.: "Decay–accelerating factor (CD55) protects human immunodeficiency virus type 1 from inactivation by human complement".
Immunology, vol. 73, 1991, pp. 377–382, G.T. Spear et al.: "Human immunodeficiency virus (HIV)–infected cells and free virus directly activate the classical complement pathway in rabbit, mouse and guinea–pig sera activation results in virus neutralization by virolysis".
Proc. of the National Academy of Sciences of USA, vol. 85, Mar. 1988, pp. 1657–1661, R. Horstmann et al.: "Antiphagocytic activity of streptococcal M. protein: Selective binding of complement control protein factor H".
The Journal of Experimental Medicine, vol. 144, 1976, pp. 1147–1163, K Whaley et al.: "Modulation of the Alternative Complement Pathway by B1H Globulin".
The Journal of Experimental Medicine, vol. 146, 1977, pp. 257–270, M.K. Pangburn et al.: "Human complement C3b inactivator: Isolation, characterization, and demonstration of an absolute requirement for the serum protein B1H for cleavage of C3b and C4b in solution".
Journal of Biochemistry, vol. 232, 1985, pp. 841–850, J. Alsenz et al.: "Structural and functional analysis of the complement component factor H with the use of different enzymes and monoclonal antibodies of factor H".
The Journal of Immunology, vol. 155, 1995, pp. 348–356, D. Gordon et al.: "Identification of Complement Regulatory Domains in Human Factor H".
AIDS, vol. 9, No. 1, 1995, pp. 19–26, H. Stoiber et al.: "Interaction of several complement proteins with gp120 and gp41, the two envelope glycoproteins of HIV–1".
Immunobiology, vol. 193, 1995, pp. 98–113, H. Stoiber et al.: "Human Complement Proteins C3b, C4b, Factor H and properdin react with specific Sites in gp120 and gp41, the envelope proteins of HIV–1".

(List continued on next page.)

*Primary Examiner*—Bennett Celsa
(74) *Attorney, Agent, or Firm*—Lorusso & Loud

(57) ABSTRACT

Pathogen-specific peptide chains are provided which prevent pathogens from escaping complement-mediated lysis. The peptide chains bind to known binding sites on pathogens to which complement regulators such as complement Factor H bind. By occupying the binding sites and thereby preventing the binding of the complement regulators to the pathogen, the peptides prevent the pathogen from blocking or suppressing the function of the complement regulators in the complement-mediated lysis process.

9 Claims, 4 Drawing Sheets

OTHER PUBLICATIONS

The Journal of Experimental Medicine, vol. 183, Jan. 1996, pp. 307–310, H. Stoiber et al.: "Efficient Destruction of Human Immunodeficiency Virus in Human Serum by Inhibiting the Protective Action of Complement Factor H and Decay Accelerating Factor (DAF, CD55)".

Science, vol. 232, Apr., 1996, pp. 341–347, B. Merrifield, "Solid Phase Synthesis".

Tetrahedron Letters, vol. 30, No. 15, 1989, pp. 1927–1930, R. Knorr et al.: "New Coupling Reagents in Peptide Chemistry".

Journal of Organic Chemistry, vol. 37, No. 22, 1972, L. Carpino and G. Han, "The 9–Fluorenylmethoxycarbonyl Amino–Protecting Group".

International Journal of Peptide & Protein Research, vol. 42, 1993, pp. 259–263, D. Knapp et al.: "Small–scale multiple peptide synthesis system".

International Journal of Peptide & Protein Research, vol. 36, 1990, pp. 255–266, D. King et al.: "A cleavage method which minimizes side reactions following Fmoc solid phase peptide synthesis".

* cited by examiner

| SEQ. I.D.# | | |
|---|---|---|
| 1 | SCR13 | Ala Ile Asp Lys Leu Lys Lys Cys Lys Ser Ser Asn Leu Ile Ile Leu Glu Glu His Leu Lys Asn Lys Lys Glu Phe Asp His Asn Ser Asn<br>                  5                            10                  15                    20                    25<br>Ile Arg Tyr Arg Cys Arg Gly Lys Glu Gly Trp Ile His Thr Val Cys Ile Asn Gly Arg Trp Asp Pro Glu Val Asn Cys Ser Met Ala Gln<br> 30                   35                    40                    45                    50                    55<br>Ile Gln Leu<br>   60 |
| 2 | a11 | Lys Cys Lys Ser Ser Asn Leu Ile Ile Leu Glu Glu His<br>                10                  15 |
| 3 | a12 | Ser Ser Asn Leu Ile Ile Leu Glu Glu His Leu Lys Asn Lys<br>       10                  15                20 |
| 4 | a13 | Ile Leu Glu Glu His Leu Lys Asn Lys Lys Glu Phe Asp His<br> 15                  20                  25 |
| 5 | a14 | Leu Lys Asn Lys Lys Glu Phe Asp His Asn Ser Asn Ile Arg<br>  20                25                30 |
| 6 | b11 | Glu Phe Asp His Asn Ser Asn Ile Arg Tyr Arg Cys Arg<br>   25               30              35 |
| 7 | b12 | Asn Ser Asn Ile Arg Tyr Arg Cys Arg Gly Lys Glu Gly Trp<br>    30              35                40 |
| 8 | b13 | Arg Cys Arg Gly Lys Glu Gly Trp Ile His Thr Val<br>     35             40              45 |
| 9 | b14 | Gly Lys Glu Gly Trp Ile His Thr Val Cys Ile Asn Gly Arg<br>    40              45                50 |

```
10  a1  Cys Val Ala Ile Asp Lys Leu Lys Lys Cys Lys Ser Ser Asn Leu Ile Ile Leu Glu Glu His
                        5               10              15
11  a2  Asp Lys Leu Lys Lys Cys Lys Ser Ser Asn Leu Ile Ile Leu Glu Glu His Leu Lys Asn Lys
                    5               10              15              20
12  a3  Cys Lys Ser Ser Asn Leu Ile Ile Leu Glu Glu His Leu Lys Asn Lys Glu Phe Asp His
                    10              15              20              25
13  a4  Leu Ile Ile Leu Glu Glu His Leu Lys Asn Lys Glu Phe Asp His Asn Ser Asn Ile Arg
                    15              20              25              30
14  b1  Glu Glu His Leu Lys Asn Lys Glu Phe Asp His Asn Ser Asn Ile Arg Tyr Arg Cys Arg
                20              25              30              35
15  b2  Asn Lys Lys Glu Phe Asp His Asn Ser Asn Ile Arg Tyr Arg Cys Arg Gly Lys Gly Trp
                25              30              35              40
16  b3  Phe Asp His Asn Ser Asn Ile Arg Tyr Arg Cys Arg Gly Lys Gly Trp Ile His Thr Val
                30              35              40              45
17  b4  Asn Ile Arg Tyr Arg Cys Arg Gly Lys Gly Trp Ile His Thr Val Cys Ile Asn Gly Arg
                35              40              45              50
18  A   Ala Ile Asp Lys Leu Lys Lys Cys Lys Ser Ser Asn Leu Ile Ile Leu Glu Glu His Leu Lys Asn Lys Glu Phe Asp His Asn Ser
                    5               10              15              20              25
19  B   Ile Arg Tyr Arg Cys Arg Gly Lys Gly Trp Ile His Thr Val Cys Ile Asn Gly Arg Trp Asp Pro Glu Val Asn Cys Ser
                    35              40              45              50              55
```

| dose of labelled peptide A (ng/well) | solid phase HIV peptides | | | |
|---|---|---|---|---|
| | SA2 | #18 | #12 | #53 |
| 0 | 0.05 | 0.05 | 0.05 | 0.05 |
| 10 | 0.340 | 0.700 | 0.650 | 0.1 |
| 100 | 1,100 | 1,500 | 1,500 | 0.08 |
| 200 | 1,500 | 2,400 | 2,080 | 0.1 |

FIG. 2

```
                        SEQUENCE LISTING (1) GENERAL INFORMATION:

(iii) NUMBER OF SEQUENCES: 25

(2) INFORMATION FOR SEQ ID NO:1:

(i) SEQUENCE CHARACTERISTICS:
         (A) LENGTH: 65 amino acids
         (B) TYPE: amino acid
         (C) STRANDEDNESS: single
         (D) TOPOLOGY: linear (ii) MOLECULE TYPE: protein (xi) SEQUENCE DESCRIPTION: SEQ ID NO:1:

Ala Ile Asp Lys Leu Lys Lys Cys Lys Ser Ser Asn Leu Ile Ile Leu
1               5                   10                  15

Glu Glu His Leu Lys Asn Lys Lys Glu Phe Asp His Asn Ser Asn Ile
            20                  25                  30

Arg Tyr Arg Cys Arg Gly Lys Glu Gly Trp Ile His Thr Val Cys Ile
        35                  40                  45

Asn Gly Arg Trp Asp Pro Glu Val Asn Cys Ser Met Ala Gln Ile Gln
    50                  55                  60

Leu
65

(2) INFORMATION FOR SEQ ID NO:2:

(i) SEQUENCE CHARACTERISTICS:
         (A) LENGTH: 14 amino acids
         (B) TYPE: amino acid
         (C) STRANDEDNESS: single
         (D) TOPOLOGY: linear (ii) MOLECULE TYPE: protein (xi) SEQUENCE DESCRIPTION: SEQ ID NO:2:

Lys Lys Cys Lys Ser Ser Asn Leu Ile Ile Leu Glu Glu His
1               5                   10

(2) INFORMATION FOR SEQ ID NO:3:
```

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:3:

Ser Ser Asn Leu Ile Ile Leu Glu Glu His Leu Lys Asn Lys
1               5                   10

(2) INFORMATION FOR SEQ ID NO:4:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:4:

Ile Leu Glu Glu His Leu Lys Asn Lys Lys Glu Phe Asp His
1               5                   10

(2) INFORMATION FOR SEQ ID NO:5:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:5:

Leu Lys Asn Lys Lys Glu Phe Asp His Asn Ser Asn Ile Arg
1               5                   10

(2) INFORMATION FOR SEQ ID NO:6:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:6:

Lys Glu Phe Asp His Asn Ser Asn Ile Arg Tyr Arg Cys Arg
1               5                   10

(2) INFORMATION FOR SEQ ID NO:7:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:7:

Asn Ser Asn Ile Arg Tyr Arg Cys Arg Gly Lys Glu Gly Trp
1               5                   10

(2) INFORMATION FOR SEQ ID NO:8:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:8:

```
Arg Tyr Arg Cys Arg Gly Lys Glu Gly Trp Ile His Thr Val
1               5                   10
```

(2) INFORMATION FOR SEQ ID NO:9:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:9:

```
Gly Lys Glu Gly Trp Ile His Thr Val Cys Ile Asn Gly Arg
1               5                   10
```

(2) INFORMATION FOR SEQ ID NO:10:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:10:

```
Cys Val Ala Ile Asp Lys Leu Lys Lys Cys Lys Ser Ser Asn Leu Ile
1               5                   10                  15
Ile Leu Glu Glu His
            20
```

(2) INFORMATION FOR SEQ ID NO:11:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:11:

```
Asp Lys Leu Lys Lys Cys Lys Ser Ser Asn Leu Ile Ile Leu
1               5                   10
Glu Glu His Leu Lys Asn Lys
15                  20
```

(2) INFORMATION FOR SEQ ID NO:12:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:12:

Cys Lys Ser Ser Asn Leu Ile Ile Leu Glu Glu His Leu Lys Asn Lys
1               5                   10                  15

Lys Glu Phe Asp His
            20

(2) INFORMATION FOR SEQ ID NO:13:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:13:

Leu Ile Ile Leu Glu Glu His Leu Lys Asn Lys Lys Glu Phe Asp His
1               5                   10                  15

Asn Ser Asn Ile Arg
            20

(2) INFORMATION FOR SEQ ID NO:14:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:14:

Glu Glu His Leu Lys Asn Lys Lys Glu Phe Asp His Asn Ser Asn Ile
1               5                   10                  15

Arg Tyr Arg Cys Arg
            20

(2) INFORMATION FOR SEQ ID NO:15:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:15:

Asn Lys Lys Glu Phe Asp His Asn Ser Asn Ile Arg Tyr Arg Cys Arg
1               5                   10                  15

Gly Lys Glu Gly Trp
            20

(2) INFORMATION FOR SEQ ID NO:16:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:16:

```
Phe Asp His Asn Ser Asn Ile Arg Tyr Arg Cys Arg Gly Lys Glu Gly
1               5                   10                  15

Trp Ile His Thr Val
            20
```

(2) INFORMATION FOR SEQ ID NO:17:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:17:

```
Asn Ile Arg Tyr Arg Cys Arg Gly Lys Glu Gly Trp Ile His Thr Val
1               5                   10                  15

Cys Ile Asn Gly Arg
            20
```

(2) INFORMATION FOR SEQ ID NO:18:

(i) SEQUENCE CHARACTERISTICS:
        (A) LENGTH: 30 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:18:

```
Ala Ile Asp Lys Leu Lys Lys Cys Lys Ser Ser Asn Leu Ile Ile
1               5                   10                  15

Leu Glu Glu His Leu Lys Asn Lys Lys Glu Phe Asp His Asn Ser
                20                  25                  30
```

(2) INFORMATION FOR SEQ ID NO:19:

(i) SEQUENCE CHARACTERISTICS:
        (A) LENGTH: 28 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:19:

```
Ile Arg Tyr Arg Cys Arg Gly Lys Glu Gly Trp Ile His Thr Val Cys
1               5                   10                  15

Ile Asn Gly Arg Trp Asp Pro Glu Val Asn Cys Ser
                20                  25
```

(2) INFORMATION FOR SEQ ID NO:20:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:20:

```
His Glu Asp Ile Ile Ser Leu Trp Asp Gln Ser Leu Lys Pro Cys
1               5                   10                  15
```

(2) INFORMATION FOR SEQ ID NO:21:

(i) SEQUENCE CHARACTERISTICS:
        (A) LENGTH: 26 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:21:

```
Asn Lys Ser Leu Glu Gln Ile Val Asn Asn Met Thr Trp Met Glu Trp
1               5                   10                  15

Asp Arg Glu Ile Asn Asn Thr Tyr Thr Ser
            20                  25
```

(2) INFORMATION FOR SEQ ID NO:22:

(i) SEQUENCE CHARACTERISTICS:
        (A) LENGTH: 24 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:22:

```
Leu Ile Glu Glu Ser Gln Asn Gln Gln Glu Lys Asn Glu Gln Glu Leu
1               5                   10                  15

Leu Glu Leu Asp Lys Trp Ala Ser
            20
```

(2) INFORMATION FOR SEQ ID NO:23:

(i) SEQUENCE CHARACTERISTICS:
        (A) LENGTH: 25 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:23:

```
Ala Arg Gln Leu Leu Ser Gly Ile Val Gln Gln Gln Asn Asn Leu Leu
1               5                   10                  15

Arg Ala Ile Glu Ala Gln Gln His Leu
            20                  25
```

(2) INFORMATION FOR SEQ ID NO:24:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:24:

```
Lys Ser Ser Asn Leu
1               5
```

(2) INFORMATION FOR SEQ ID NO:25:

(i) SEQUENCE CHARACTERISTICS:
        (A) LENGTH: 5 amino acids
        (B) TYPE: amino acid -continued

```
        (C) STRANDEDNESS: single
        (D) TOPOLOGY: linear (ii) MOLECULE TYPE: protein (xi) SEQUENCE DESCRIPTION: SEQ ID NO:25:

His Asn Ser Asn Ile
1               5
```

INHIBITION OF BINDING OF COMPLEMENT FACTOR H

BACKGROUND OF THE INVENTION (1) Field of the Invention

This invention relates generally to peptide chains used to block binding sites on pathogens and more particularly to peptide chains used to block binding sites for Complement Factor H (CFH) on pathogens such as the Human Immunodeficiency Virus (HIV).

(2) Description of Related Art

Various pathogens, like HIV, have evolved the ability to escape from complement-mediated lysis. See, e.g., Marschang P. Sodroski J., Wurzner R. and Dierich M. P., "Decay-accelerating Factor (CD55) Protects Human Immunodeficiency Virus Type 1 From Inactivation by Human Complement," Eur. J. Immunol. 25: 285–90 (1995) and Horstmann, R. D., Sievertsen, H. J., Knobloch, J. and Fischetti, V. A., "Antiphagocytic Activity of Streptococcal M Protein: Selective Binding of Complement Control Protein Factor H," Proc. Nat'l. Acad. Sci. U.S.A. 85: 1657–1661 (1988). The complement system is part of the immune system. Its main functions are the opsonisation of micro-organisms to allow more efficient phagocytosis and complement-mediated lysis of pathogens. To turn down the activity of complement and to protect host cells from unspecific damage, regulators of complement activity (RCA's) are required. Among this family of negative regulators is CFH, a very abundant plasma protein. CFH has been shown to down-regulate the alternative pathway of complement activation by directly affecting the formation and stability of C3 and C5 convertase and by acting as a cofactor for the cleavage of C3b into its inactive form iC3b as described by Whaley, K. and Ruddy, S., "Modulation of the Alternative Complement Pathway by β1H Globulin," J. Exp. Med. 144: 1147 (1976) and Pangburn, M. K., Schreiber and Eberland, H. J. Muller, "Human Complement C3b Inactivator: Isolation, Characterization and Demonstration of an Absolute Requirement for the Serum Protein β1H for Cleavage of C3b and C4b in Solution," J. Exp. Med. 146:257 (1977). Responsible for these effects is a functional site located in the first 5 short consensus repeats (SCR 1–5) of CFH as described in Alsenz, J., Lambris, J. D., Schulz, T. F. and Dierich, M. P., "Localization of the Complement Component C3b-binding Site and the Cofactor Activity for Factor I in the 38-kDa Tryptic Fragment of Factor H," Biochem. J. 224: 389 (1984) and Gordon, D. L., Kaufman, R. M., Blackmore, T. K., Kwong, J. and Lublin, D. M., "Identification of Complement Regulatory Domains in Human Factor H," J. Immunol. 155: 348 (1995). An interaction site for polyanionic molecules has been mapped in SCR 13. Pangburn, M. K., Atkinson, M. A. and Meri, S., "Localization of the Heparin-binding Site on Complement Factor H," J. Biol. Chem. 266: 16847 (1991). For example, SCR 13 has been shown to bind streptococcal protein M and is responsible for protection of M+ strains from complement-mediated bactericidal activity. See Horstmann et al. article, above. Recently, additional binding regions for negatively-charged particles in SCR 7 have also been described. Blackmore, T. and Gordon, D., "SCR 7 is a Major Heparin/Sialic Acid Binding Site of Complement Factor H," J. Mol. Immunol. 33 (S1): 15 (1996). It is believed that SCR 7 is a potential binding site for host cells.

Applicants have recently shown the CFH interacts with specific sites on the envelope of HIV. Specifically, envelope glycoproteins, gp120 and gp41, have been demonstrated to be binding sites for CFH. See Stoiber, H., Ebenbichler, C., Schneider, R., Janatova, J. and Dierich, M. P., "Interaction of Several Complement Proteins with gp120 and gp41, the Two Envelope Glycoproteins of HIV-1," AIDS 9:19 (1995) and Pinter, C., Siccardi, A. G., Longhi, R. and Clivio, A., "Direct Interaction of Complement Factor H with the C1 Domain of HIV Type 1 Glycoprotein 120," AIDS Research & Human Retroviruses 11: 577 (1995). Incubation of free HIV or HIV-infected cells with sera that has been depleted of CFH (NHS$^{CFH-}$) results in the complement-mediated virolysis of primary HIV isolates and the killing of HIV-infected cells. Re-titration of CFH to NHS$^{CFH-}$ reconstitutes the resistance of HIV against complement-mediated destruction. See Stoiber, H., Pinter, C., Siccardi, A. G., Clivio, A. and Dierich, M. P., "Efficient Destruction of Human Immunodeficiency Virus in Human Serum by Inhibiting the Protective Action of Complement Factor H and Decay Accelerating Factor (DAF, CD55)," J. Exp. Med. 183: 307 (1996).

In addition, Applicants have shown that the antibody 2F5, described by Katinger et al. (See WO95/07354 A1) interacts with a CFH binding site in gp41. From this information, the Applicants hypothesized that one of the HIV-neutralizing effects of this antibody is due to the inhibition of CFH interaction with gp41, resulting in complement-mediated lysis of the virus.

The present invention is based on the assumption that if the hypothesis described above is correct, it is not necessary to use an antibody for specifically blocking the binding sites on pathogens. Using a molecule which is able to block sites on pathogens which act as binding sites for CFH should have the same or even more promising effects.

SUMMARY OF THE INVENTION

It is accordingly an object of the invention to eliminate the need for antibody-mediated pathogen destruction. It is a further object of the invention to provide a pathogen specific peptide chain that binds to the sites that would otherwise be available to bind CFH so that CFH-mediated lysis of pathogens is not prevented.

It is a still further object of the invention to provide a peptide chain that does not have the active sites of CFH and does not have the binding sites on CFH that bind to host cells to regulate complement activity.

By screening with specific peptides, Applicants have discovered that CFH binding on pathogens can be inhibited so that complement-mediated destruction of the pathogens is induced. The Applicants have discovered that binding inhibition can be accomplished with peptides containing less than 100 amino acids. The amino acid chains, SEQ. ID NO: 1, were derived from the SCR 13 region of CFH. Whole CFH has been modified so that the areas involved in mediating the interaction with pathogens are conserved while the areas responsible for inhibition of complement-mediated lysis are deleted. Additionally, areas believed to be involved in binding to host cells such as SCR7 have also been deleted to provide a pathogen-specific peptide chain.

Such pathogen-specific peptide chains can be synthesized in a variety of ways including mutation and expression of mutated CFH DNA. Using known peptide synthesis procedures, it is even possible to use cyclic peptides or introduce D-amino acids which can result in higher resistance of the peptide chain to degradation by human serum.

By screening peptide and pseudopeptide libraries, the invention offers the possibility to detect in addition to the described peptides, other molecules which interfere with CFH binding on various pathogens. The effect of those substances can be easily checked by incubating pathogen which are resistant to human serum with antibodies specific against the pathogen, serum and peptides or pseudopeptides followed by testing and analyzing for the presence of complement-mediated lysis of the pathogen.

BRIEF DESCRIPTION OF THE DRAWINGS

FIG. 1A is a depiction of SEQ. ID NO: 1 and modified variants thereof resulting from selective deletions.

FIG. 1B is a continuation of FIG. 1A.

FIG. 2 depicts the results of the binding of biotin-labelleci peptide A to HIV-derived peptides with the values being expressed as absorbance at 492 nm.

FIG. 3 is a bar graph showing the effect of SEQ. ID NO: 1 on complement-dependent cytotoxicity induced on HIV-infected cells.

DESCRIPTION OF THE PREFERRED EMBODIMENTS

As shown in FIGS. 1A–1B, peptides A and B were synthesized with the step-wise solid-phase method described in Merrifield, R. B., "Solid-phase Peptide Synthesis," Science 232: 341 (1986), on an Abi 433A Peptide Synthesizer (Applied Biosystems, Foster City, Calif.) at a scale of 0.1 mmole. The overlapping peptides, 17 mer in length, including Gly at the amino terminus as the spacer and Glycyl-Tyrosine at the carboxy terminus to enable spectrophotometric quantitation were synthesized manually at a scale of 0.02 mmoles on NovaSyn TGA resin using chemical protocols based on the Fmoc strategy, Knorr, R., Trzeciak, A., Bannwarth, W. and Gillessen, D., "New Coupling Reagents in Peptide Chemistry," Tetrahedron Lett. 30:1927 (1989), and in situ amino acid activation, Carpino, L. A. and Han, G. Y., "The 9-Fluorenylmethoxycarbonyl Amino Protecting Group," J. Org. Chem. 37:3404 (1972). The apparatus for the manual, small scale simultaneous multiple peptide synthesis was essentially that described by Knapp in Knapp, D. R., Oatis, J. E. and Papac, D. I., "Small-scale Manual Multiple Peptide Synthesis System," Int. J. Peptide Protein Res. 42:259 (1972). Resins, N-α-9-fluorenylmethoxycarbonyl amino acids (side chain protected) and activating reagents such as 2-(1H-Benzotriazole-1-yl)1,1,3,3-tetramethyluronium tetrafluoroborate (HBTU) and N-Hydroxybenzotriazole (HOBt) were purchases from Novabiochem (Laufelfingen, Switzerland). A ten-fold excess of active reagent over the amino terminal content of the resin was used both in the automatic and in the manual peptide synthesis. After assembly, the completed peptides were fully de-protected and removed from the solid support according to the cleavage method suggested by King in King, D. S., Fields, C. G. and Fields, G. B., "A cleavage Method Which Minimizes Side Reactions Following Fmoc Solid Phase Peptide Synthesis," Int. J. Pept. Protein. Res. 36: 255 (1990). The free peptides were repeatedly lyophilized from water and analyzed by reverse phase liquid chromatography (RF-HPLC), to assess their homogeneity. Amino acid analysis was carried out on all the peptide preparations before use. The peptides of FIGS. 1A–1B were used in the immunometric assay both before and after purification.

Synthetic peptides with different lengths and overlapping patterns of the whole SEQ. ID NO: 1 were used as shown in FIGS. 1A–1B. "Mutagenized" peptides using alanine as a substitute for the naturally occurring amino acids in critical positions of SCR 13 of CFH were also produced. Finally, amino acids contained in the known active regions of CFH were scrambled to check the sequence dependence and specificity of the peptide biologic activity.

Regarding the HIV envelope peptides, only #SA2 (His Glu Asp Ile Ile Ser Leu Trp Asp Gln Ser Leu Lys Pro Cys, Env. 105–119) Sequence I.D. #20, of the gp120-derived peptides, described by Pinter in the AIDS Research & Human Retroviruses article referenced above as being the target of CFH binding, was used in this study to reproduce the CFH-gp120 interaction. Peptides #18 (Asn Lys Ser Leu Glu Gln Ile Val Asn Asn Met Thr Trp Met Glu Trp Asp Arg Glu Ile Asn Asn Thr Tyr THr Ser, Env. 621–645) Sequence I.D. #21 and #12 (Leu Ile Glu Glu Ser Gln Asn Gln Gln Glu Lys Asn Glu Gln Glu Leu Leu Glu Leu Asp Lys Trp Ala Ser, Env. 650–673) Sequence I.D. #22 of the gp41-derived peptides described in Pinter, C., Siccardi, A. G., Lopalco, L., Longhi, R. and Clivio, A., "HIV Glycoprotein 41 and Complement Factor H Interact with Each Other and Share Functional as well as Antigenic Homology," AIDS Research & Human Retroviruses 11:971 (1995) as being the targets of CFH binding were used to reproduce the CFH-41gp interaction. Peptide #53 (Ala Arg Gln Leu Leu Ser Gly Ile Val Gln Gln Gln Asn Asn Leu Leu Arg Ala Ile Glu Ala Gln Gln His Leu, Env. 546–570) Sequence I.D. #23, from the gp41 ectodomain which has shown no CFH binding was used as a negative control.

Cell lines and tissue culture techniques 8E5 cells which are! chronically infected with a polymutant of LAV, uninfected CD4+CEM cells, HIV-IIIb-infected and uninfected H9 cells were obtained from the American Type Culture Collection (ATCC). Cells adapted to grow in a protein-free medium supplemented with 4 mM L-glutamine and in the absence of antibiotics (S-2897, SIGMA) as described, were maintained in a humidified $CO_2$ incubator (NAPCO). Cell density was always kept between $8\times10^5$ and $1.5\times10^6$ cells/ml.

CFH was purified as described by Pinter et al., AIDS Research & Human Retroviruses 11: 971. Briefly, normal human plasma was desalted, diluted 1:4 in buffer A (20 mM Tris-HCl pH 8.5), and fractionated by anion exchange HPLC (MA7P BioRad, Milan, Italy), and hydrophobic interaction (HI) HPLC (BioRad). The last peak eluting from the HI column contained only CFH and albumin. The albumin was removed by vacuum dialysis using 100 kDa out off membranes and subsequent concentration. This fraction contained pure CFH as determined by one- and two-dimensional SDS-polyacrylamide gel electrophoresis.

Synthetic peptides and recombinant proteins were dissolved in Carbonate-bicarbonate buffer, 50 mM, pH 9.2 at 50 $\mu$g/ml (micrograms per milliliter) and 10 $\mu$g/ml, respectively, distributed in 100 $\mu$l aliquots into flat-bottomed 96-well ELISA plates (Greiner, Germany) and left at 37° C. for 3 hours. The plates were then washed three times in phosphate-buffered saline (PBS) and the wells were overcoated with a 3% (w/v) solution of bovine serum albumin (BSA) in PBS. The CFH source (either from fresh plasma or from plasma subjected to subsequent purification steps), was diluted to the appropriate concentration (1 mg/ml) in PBS-BT (=PBS containing 1% BSA and 1% Tween 20), pH 7.0 and exposed to the solid phase for one hour at 37° C. After washing in PBS+1% Tween 20 (=PBS-T), bound CFH was detected by the use of specific, biotin-labelled MAb 5H5, Pinter et al., AIDS Research & Human Retroviruses 11: 971, and peroxidase-labelled streptavidin (Sigma, Italy). The reaction was developed with o-phenylene-diamine/$H_2O_2$ for fifteen minutes and then stopped by the addition of 4N $H_2SO_4$. Absorbance was detected at 492 $\mu$m with a MT450 microplate reader (BioRad).

Figure 3:
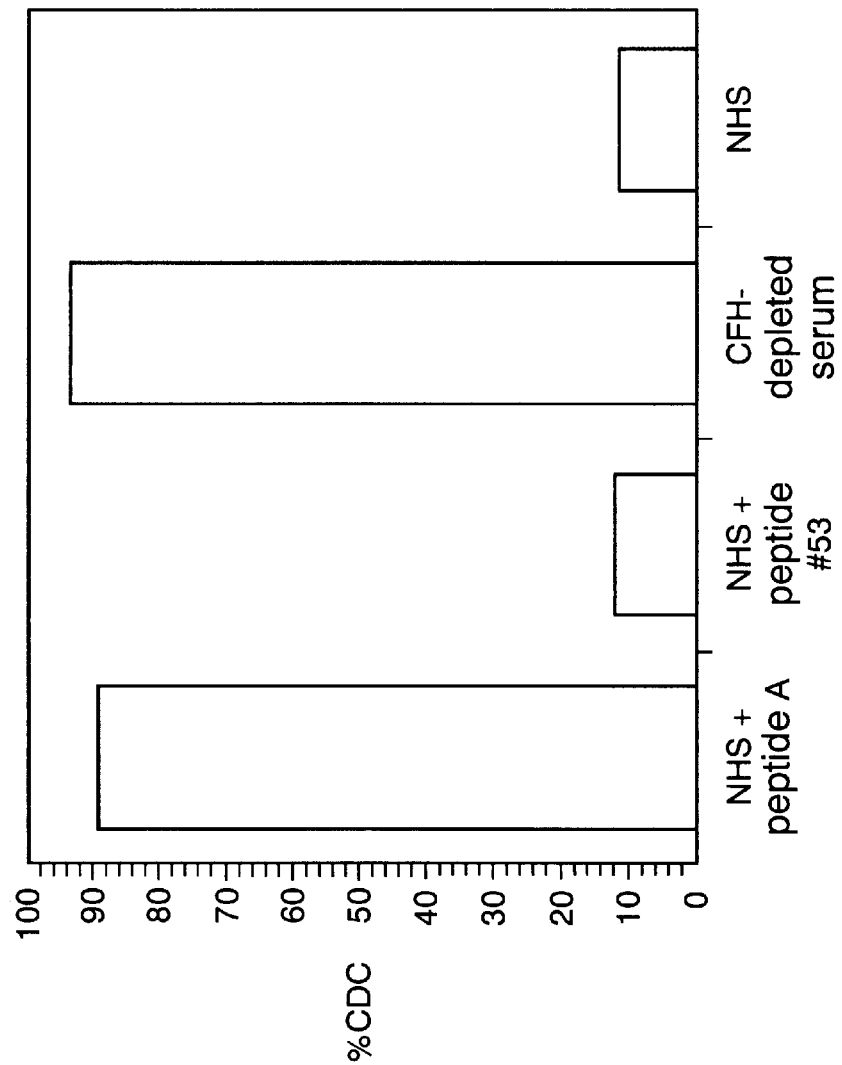

Along with the above-described assay, a preincubation assay was also conducted with peptides. The general features of this assay are essentially the same as those described for the CFH binding assay above, except that before the addition of CFH, the solid phases were preincubated for one hour with increasing concentrations of putative competitors. Peptides used as MEcompetitors were dissolved in PBS-BT with a pH of 7.0. The solid phases were washed in PBS-T and CFH was detected with the biotin-labelled MAb 5H5 as previously described.

In these experiments, the competitors were added to the solid phases simultaneously with CFH. Peptides were dissolved in PBS-BT with a pH of 7.0. Peptide concentrations ranged from 0 to 50 μg/ml. Bound CFH was detected as in the previous assay. Heparin (Sodium salt, Fluka, Germany) was dissolved in PBS-T at 50 mg/ml as a stock solution and then further diluted in the assays.

To test for induction of complement-dependent, HIV-specific cytolysis by SEQ. ID NO: 1 peptides, a complement-dependent cytolytic assay similar to the one described in Stoiber et al., J. Exp. Med. 183: 307, was used to check the possibility of inhibiting the HIV-CFH interaction with the addition of exogenous reagents. To construct this assay, chronically HIV-infected 8E5 cells and uninfected CEM cells were preincubated with antibodies from AIDS sera (AIDS Ig) or from normal human serum (NHS Ig) and incubated with human serum (1:10 diluted) as the complement source in the presence, or in the absence, of exogenously added, putative inhibitors of the CFH-HIV interaction. Complement-dependent cytolysis (CDC) was detected by counting viable cells in 24-well short term (1b-exposure) cultures. Serum depleted of CFH was used as the positive CDC control.

Since three HIV envelope-derived peptides have been previously identified as targets of CFH binding, these peptides (#SA2, Sequence I.D. #20; #18 Sequence I.D. #21; and #12Sequence I.D. #22) were fixed on ELISA plates and used as CFH "catchers," in the absence of, and in the presence of, putative competitors. Two relatively long peptides (A and B as shown in FIG. 1B), which comprise the majority of SEQ. ID NO: 1, the sequence of which was derived from the Swiss-Prot database, were used as a first glance analysis aimed at restricting the region of SEQ. ID NO: 1 which interacts with HIV. Peptide A Sequence I.D. #18, is a 30 residue peptide representing the N-proximal region of SEQ. ID NO: 1. Peptide B Sequence I.D. #19 is a 28-mer spanning the rest of the sequence, with the exception of the Asparagine in position 775. Both peptides were used to compete with the interaction of CFH with the HIV target sequences. Heparin was used as the positive competition control. The primary reason SEQ. ID NO: 1 has been selected for testing is due to previous work described in Pinter et al., AIDS Research & Human Retroviruses 11:577, in which it was found that heparin inhibited the binding of CFH to HIV and to the target peptides.

Peptide A Sequence I.D. #18, competed very efficiently with the binding of CFH to the three envelope peptides used. This result suggests that the same region of SCR 13 Sequence I.D. #1 is involved in the binding to the target sequences in gp120 and gp41. The inhibition was due to the interaction of peptide A Sequence I.D. #18, with the solid phase. Preincubation of the target peptides with peptide A Sequence I.D. #18 before performing the assay gave the same effect as simultaneous competition. Peptide B Sequence I.D. #19 had almost no effect. Heparin competed only when incubated simultaneously with CFH, as expected, but was inactive in preincubation experiments.

To better localize the CFH binding site, more detailed competition assays were performed with the whole set of short overlapping 14-mer and 21-mer synthetic peptides of SEQ. ID NO: 1 as shown in FIGS. 1A–1B. Regarding the 21-mer peptides, maximum competition was demonstrated by peptides a2 Sequence I.D. #11, b1 Sequence I.D. #14 and b2 Sequence I.D. #15 which define two regions of SCR 13 Sequence I.D. #1, that are involved in binding to the HIV envelope peptides. Regarding the 14-mer peptides, b11 Sequence I.D. #6, and b12 Sequence I.D. #7 retained all the inhibitory capacity of their corresponding 21-mer peptide chains, b1 Sequence I.D. #14 and b2 Sequence I.D. #15. In contrast, the short peptide chains corresponding to the longer 21-mer a2 Sequence I.D. #11, peptide chain, did not demonstrate competition with the binding of CFH to the HIV envelope peptides thereby indicating with regard to these short peptide chains, that the region of interaction may be more extended, or that a particular peptide conformation is required for binding.

Peptide A Sequence I.D. #18, labelled with biotin during synthesis as previous described, was used to confirm the interaction observed in the competition assays. The results are shown in FIG. 2. This peptide, being used as a tracer, was able to bind efficiently to the gp120 peptide #SA2 Sequence I.D. #20, and to the gp41 peptides #12 Sequence I.D. #22 and #18 Sequence I.D. #21. This interaction was competed by peptide A itself, by the envelope peptides #SA2 Sequence I.D. #20, #12 Sequence I.D. #22 and #18 Sequence I.D. #21 but not by peptide #53 Sequence I.D. #22. Therefore, the three HIV-derived peptides seem to share functional homology with respect to the interaction with CFH since they all bind to the same region on SEQ. ID NO: 1. Peptide b11 Sequence I.D. #6 has been shown to inhibit the binding of peptide A Sequence I.D. #18, and the purified CFH molecule to all three HIV-derived target peptides.

To better define the regions of SCR 13 Sequence I.D. #1, responsible for the binding of HIV, the peptide b11 was modified during synthesis as follows:

a) Alanine was substituted for the naturally occurring amino acids;

b) The putative active sequence, His Asn Ser Asn Ile Sequence I.D. #25, was scrambled and the flanking sequences were left unchanged;

c) The putative active sequence of region I (Lys Ser Ser Asn Leu, Sequence I.D. #24) was grafted into peptide b11 Sequence I.D. #6 in substitute of the original His Asn Ser Asn Ile, Sequence I.D. #25, core;

d) The two amino acids flanking the active box of peptide b11 and the active box of the "grafted" peptide were substituted with cysteines and covalently closed.

All of these peptides were used to compete with CFH binding to the HIV target peptides. The results of an "alanine" scan indicate that mutations within the core sequence of peptide b11 totally abolish the ability of the peptides to compete with CFH binding. The data also indicate that the flanking sequences also contribute to the peptide activity since mutations in these regions decrease the competing capacity of the resulting peptides.

The scrambled peptide suggests that the sequences flanking the central box do not participate in the binding to HIV; this peptide contains unmodified flanking sequences and its core contains the naturally occurring amino acids randomly sorted. It is clear that the core must contain the natural sequence to be able to compete with CFH binding. It is also clear that the flanking sequences are unable to compete by themselves. The core of region I (Lys Ser Ser Asn Leu, Sequence I.D. #24) and that of region II (His Asn Ser Asn Ile, Sequence I.D. #25) were shown to be functionally homologous. When the core of region I was grafted into the flanking sequences of peptide b11 Sequence I.D. #6 (FIG. 1A), partial competition was readily observed.

$^{125}$I-labelled CFH was used to show that in addition to binding to recombinant gp41, Stoiber, H., Schneider, R., Janatova, J. and Dierich, M. P., "Human Complement Proteins C3b, C4b, Factor H and Properdin React with Specific Sites in gp120 and gp41, the Envelope Proteins of HIV-1," Immunobiology 193: 98 (1995) and Pinter et al., AIDS Research & Human Retroviruses 11: 971, and to envelope-derived synthetic peptides in ELISA, CFH is also able to interact with envelope proteins at the surface of HIV-infected cells. A significant difference in the efficiency of CFH binding between infected compared to uninfected cells was observed. As a control, the binding of $^{125}$I-labelled CFH was inhibited using cold CFH. The ELISA assays with immobilized rsgp41 gave similar results. The standard deviation in these assays was below 15%.

Based on the results of the binding assays on intact cells, and on the Applicants' previous observation that CFH depletion results in HIV-specific complement-dependent cytolysis, Stoiber et al., J. Exp. Med. 183: 307, the possibility of blocking the intrinsic HIV-infected cell resistance to complement lysis by the addition of exogenous inhibitors of the CFH-HIV envelope protein interaction was checked. Peptide A Sequence I.D. #18, as a representative of CFH inhibitors, was used as the competitor in the CDC assay described above and in Stoiber et al., J. Exp. Med. 183: 307. As shown in FIG. 3, the presence of peptide A Sequence I.D. #18 in the incubation mixture resulted in highly efficient CDC induction which was similar to that of the CFH-depleted control.

It is to be understood that the present invention is by no means limited to the particular peptide sequences constructions herein disclosed and/or shown in the drawings, but also comprises any modifications or equivalents within the scope of the claims.

What is claimed is:

1. A reagent composition for the treatment of diseases caused by pathogens to which human Complement Factor H binds, wherein the reagent composition is a peptide chain comprising SEQ. I.D. NO. 1 and consisting of less than 100 amino acids, wherein said peptide chain binds to at least one of a pathogen's Complement Factor H-binding regions.

2. A reagent composition for the treatment of diseases caused by pathogens to which human Complement Factor H binds, wherein the reagent composition is a peptide chain consisting of less than 100 amino acids and comprising a member selected from the group consisting of: SEQ. I.D. NO. 2, SEQ. I.D. NO. 10, SEQ. I.D. NO. 11, SEQ. I.D. NO. 12, and SEQ. I.D. NO. 18, wherein said peptide chain binds to at least one of a pathogen's Complement Factor H-binding regions.

3. A reagent composition for the treatment of diseases caused by pathogens to which human Complement Factor H binds, wherein the reagent composition is a peptide chain consisting of less than 100 amino acids and comprising a member selected from the group consisting of: SEQ. I.D. NO. 5, SEQ. I.D. NO. 6, SEQ. I.D. NO. 13, SEQ. I.D. NO. 14, SEQ. I.D. NO. 15, and SEQ. I.D. NO. 16, wherein said peptide chain binds to at least one of a pathogen's Complement Factor H-binding regions.

4. A peptide selected from the group consisting of: SEQ. I.D. NO. 1, SEQ. I.D. NO. 2, SEQ. I.D. NO. 10, SEQ. I.D. NO. 11, SEQ. I.D. NO. 12, and SEQ. I.D. NO. 18 which binds to gp 41 an gp120 peptides of a Human Immunodeficiency Virus.

5. A peptide of less than 100 amino acids which includes SEQ I.D. No. 24 and SEQ I.D. No. 25 which are found in Complement Factor H and which binds to the same pathogens as Complement Factor H.

6. A peptide selected from the group consisting of: SEQ. ID. NO. 5, SEQ. ID. NO. 6, SEQ. ID. NO. 13, SEQ. ID. NO. 14, SEQ. ID. NO. 15, and SEQ. ID. NO. 16 which binds to gp 41 and gp 120 peptides of a Human Immunodeficiency Virus.

7. A compound which consists of less than 100 amino acids and includes SEQ I.D NO. 24, and SEQ. I.D. NO. 25 which are found in Complement Factor H and which binds to the same pathogens as Complement Factor H and additionally includes at least one peptide selected from the group consisting of: SEQ. ID. NO. 1, SEO. ID. NO. 2, SEQ. ID. NO. 5, SEQ. ID. NO. 6, SEQ. ID, NO. 10, SEQ. ID. NO. 11, SEQ. ID. NO. 12, SEQ. ID. NO. 13, SEQ. ID. NO. 14, SEQ. ID. NO. 15 and SEQ. ID. NO. 16 which binds to gp 41 and gp 120 peptides of a Human Immunodeficiency Virus.

8. A cyclic compound which consists of less than 100 amino acids and comprises SEQ. ID. NO. 24 and SEQ. ID. NO. 25 which are found in Complement Factor H and which binds to the same pathogens as Complement Factor H.

9. The cyclic compound of claim 8 which further comprises at least one peptide selected from the group consisting of: SEQ. ID. NO. 1, SEQ. ID. NO. 2, SEQ. ID. NO. 5, SEQ. ID. NO. 6, SEQ. ID. NO. 10, SEQ. ID. NO. 11, SEQ. ID. NO. 12, SEQ. ID. NO. 13, SEQ. ID. NO. 14, SEQ. ID. NO. 15 and SEQ. ID. NO. 16 which binds to gp 41 and gp 120 peptides of a Human Immunodeficiency Virus.

* * * * *